United States Patent [19]

Emura et al.

[11] Patent Number: 5,750,804
[45] Date of Patent: May 12, 1998

[54] PROCESS FOR PRODUCING TRANS-3-ISOCAMPHYLCYCLOHEXANOL

[75] Inventors: Makoto Emura; Takaaki Toyoda; Nobuo Seido; Makoto Harada, all of Kanagawa; Ryoji Noyori, Aichi; Takao Ikariya, Aichi; Takashi Ohkuma, Aichi, all of Japan

[73] Assignee: Takasago International Corporation, Tokyo, Japan

[21] Appl. No.: 813,238

[22] Filed: Mar. 7, 1997

[30] Foreign Application Priority Data

Mar. 7, 1996 [JP] Japan .................. 8-050309

[51] Int. Cl.$^6$ .................................. C07C 35/08
[52] U.S. Cl. ........................... 568/834; 568/832
[58] Field of Search ................... 568/834, 832; 562/326

[56] References Cited

FOREIGN PATENT DOCUMENTS 834593  3/1952  Germany .

OTHER PUBLICATIONS

E. Demole, *Helv. Chem. Acta*, vol. 47, pp. 319–388 (1964).
E. Demole, *Helv. Chem. Acta*, vol. 47, pp. 1766–1774 (1964).
G. Buchbauer et al, *Helv. Chem. Acta*, vol. 77, pp. 2286–2296 (1994).
G.K. Lange et al, *Conference Proceeding of Fragrance Flavor Subst. Proc. Int.*, Haarmann Reimer Symp., pp. 111–121 (1980).
E. Demole, *Helv. Chem. Acta*, vol. 52, pp. 2065–2085 (1969).
R.T. Dahill et al, *J. Org. Chem.*, vol. 35, pp. 251–252 (1970).
Y.M.Y. Haddad et al, *Proc. Chem. Soc.*, vol. 93, p. 361 (1964).
T. Ohkuma et al, *J. Am. Chem. Soc.*, vol. 117, pp. 10417–10418 (1995).

*Primary Examiner*—Gary Geist
*Assistant Examiner*—Karl J. Puttlitz, Jr.
*Attorney, Agent, or Firm*—Sughrue, Mion, Zinn, Macpeak & Seas, PLLC

[57] ABSTRACT

A process whereby trans-3-isocamphylcyclohexanol, which is useful as a perfume ingredient, can be produced on an industrially available scale, at a low cost and at a high stereoselectivity, is disclosed. The process comprises hydrogenating 3-isocamphylcyclohexanone represented by the following formula (I):

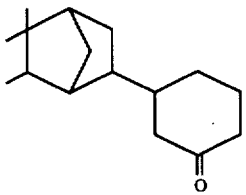

(I)

by using a ruthenium/phosphine complex as a catalyst in the presence of a base containing an alkali metal or an alkaline earth metal and an amine.

11 Claims, No Drawings

PROCESS FOR PRODUCING TRANS-3-ISOCAMPHYLCYCLOHEXANOL

FIELD OF THE INVENTION

This invention relates to a process for producing trans-3-isocamphylcyclohexanol having a specific conformation. This compound is useful as a perfume ingredient having, in particular, a sandalwood oil-like fragrance.

BACKGROUND OF THE INVENTION

Sandalwood oil, which is an essential oil obtained from sandalwood coming from the eastern part of India originally, is highly valued as a perfume ingredient. However, it is regulated from the viewpoint of the conservation of resources and environment to cut down sandalwood trees, which restricts the yield of natural sandalwood oil. Therefore, attempts have been made to develop synthetic sandalwood oil-like perfume ingredients as substitutes for natural sandalwood oil.

It is known that the major components characteristic of the fragrance of natural sandalwood oil are α-santalol and β-santalol. However, santalol can be hardly synthesized in a large amount on an industrial scale owing to its chemical structure. In recent years, there have been synthesized substances which are different from santalol in chemical structure but closely similar thereto in fragrance.

One of these substances is a product obtained by reacting camphene with guaiacol by using boron trifluoride and then hydrogenating the reaction product with the use of Raney nickel as a catalyst [West German Patent No. 834,593, (1952) (Cl. 39c, 2); and Chemical Abstracts 51:17107d (1957)]. This substance has been put into the market under several trade names such as Santalex (registered trade mark, manufactured by Takasago International Corporation, the same will apply hereinafter) in the form of a mixture with cyclohexanol substituted by isobornyl, isocamphyl or isofenchyl and utilized as a substitute for sandalwood oil.

It is reported that among the components of this mixture, trans-3-isocamphylcyclohexanol [i.e., (1S,3S)- and (1R,3R)-isocamphylcyclohexanol] the most strongly affects the sandalwood oil-like fragrance, while other components have only little fragrance with poor fragrance qualities or none [E. Demole, Helv. Chim. Acta, Vol. 47, pp. 319–388 (1964)]. As the result of the comparison of the structures of α- and β-santalols which are the perfume components of sandalwood oil with 3-isocamphylcyclohexanol, it is further reported that the trans-isomer of 3-isocamphylcyclohexanol, in which the isocamphyl substituent at the 3-position of the cyclohexane ring forms an equatorial bond to the cyclohexane ring and the hydroxyl substituent at the 1-position forms an axial bond, is essentially required in the expression of the sandalwood oil-like fragrance [E. Demole, Helv. Chim. Acta, Vol. 47, pp. 1766–1774 (1964)]. Also, the calculation of conformation relating to the correlation between the structure and activity of the compound supports the above assumption that the axial bond of the hydroxyl group is essentially required in the expression of the sandalwood oil-like fragrance [G. Buchbauer et al., Helv. Chim. Acta, Vol. 77, pp. 2286–2296 (1994)].

However, the marketed mixtures as described above contain only about 8% by weight of trans-3-isocamphylcyclohexanol [G. K. Lange et al., Conference Proceeding of Fragrance Flavor Subst. Proc. Int., Haarmann Reimer Symp., pp. 111–121 (1980)]. Accordingly, there have been proposed some methods for selectively synthesizing this trans-3-isocamphylcyclohexanol.

Examples of these methods include those undertaken via 2-isocamphylphenol [E. Demole, Helv. Chim. Acta, Vol. 52, pp. 2065–2085 (1969)] or 4-isocamphylphenol [R. T. Dahill et al., J. Org. Chem., Vol. 35, pp. 251–252 (1970)]. However, these methods are not suitable for industrial production, since many isomers are formed in the course of the synthesis and, furthermore, lithium aluminum hydride which can be hardly handled in a large amount should be employed therein.

It is also reported to synthesize trans-3-isocamphylcyclohexanol of a high purity by oxidizing a mixture of cis- and trans-3-isocamphylcyclohexanols to give 3-isocamphylcyclohexanone and then reducing the product with lithium borohydride substituted with a bulky alkyl group [G. K. Lange et al., Conference Proceeding of Fragrance Flavor Subst. Proc. Int., Haarmann Reimer Symp., pp. 111–121 (1980)]. However, neither the purity nor the yield of the trans-3-isocamphylcyclohexanol product thus obtained is reported in the reference. Moreover, this method is unsuitable for industrial production, since an expensive reagent should be employed in the reductive reaction.

There is also known a method for producing cyclohexanol having an axial bond of hydroxyl group wherein a 4-alkylcyclohexanone is stereoselectively hydrogenated by heating under reflux with chloroiridic acid and trimethyl phosphonate in isopropanol [Y. M. Y. Haddad et al., Proc. Chem. Soc., Vol. 93, p. 361 (1964)]. However, this reaction proceeds very slowly. In addition, it is reported that this method is not applicable to the reduction of 3-isocamphylcyclohexanone [G. K. Lange et al., Conference Proceeding of Fragrance Flavor Subst. Proc. Int., Haarmann Reimer Symp., pp. 111–121 (1980)].

Although there have been proposed several methods for selectively synthesizing trans-3-isocamphylcyclohexanol as described above, no industrially usable method therefor has been established so far.

Accordingly, it is an object of the present invention to provide a process whereby trans-3-isocamphylcyclohexanol, which is a component essentially required in the expression of the sandalwood oil-like fragrance, can be produced on an industrially available scale, at a low cost and at a high stereoselectivity.

SUMMARY OF THE INVENTION

To achieve the above-mentioned object, the present inventors have found out that trans-3-isocamphylcyclohexanol with a high purity can be obtained by stereoselectively hydrogenating 3-isocamphylcyclohexanone by using a catalyst containing inexpensive ruthenium in the presence of a base containing an alkali metal or an alkaline earth metal and an amine, thus completing the present invention.

Accordingly, the present invention relates to a process for producing trans-3-isocamphylcyclohexanol which comprises hydrogenating 3-isocamphylcyclohexanone represented by the following formula (I):

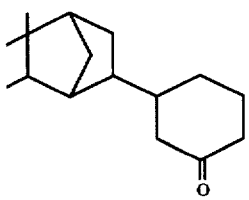

by using a ruthenium/phosphine complex as a catalyst in the presence of a base containing an alkali metal or an alkaline earth metal and an amine.

The 3-isocamphylcyclohexanone of the formula (I) can be stereochemically represented by the following formulae (Ia) and/or (Ib) (i.e., the cyclohexane ring is shown in the chair conformation):

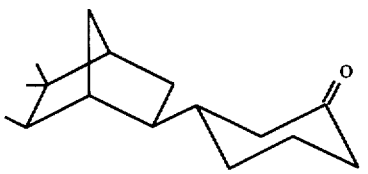
(Ia)

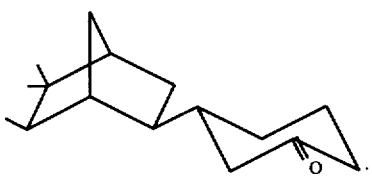
(Ib)

The trans-3-isocamphylcyclohexanol of the present invention obtained by hydrogenating the above compound includes (1S,3S)-isocamphylcyclohexanol represented by the following formula (IIa) and/or (1R,3R)-isocamphylcyclohexanol represented by the following formula (IIb):

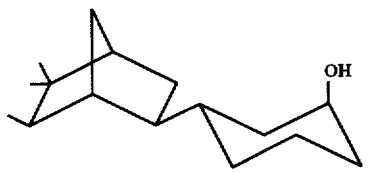
(IIa)

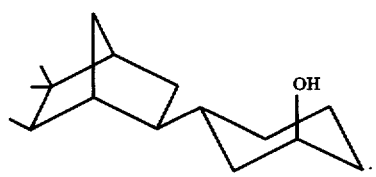
(IIb)

DETAILED DESCRIPTION OF THE INVENTION

The 3-isocamphylcyclohexanone to be used as the reaction substrate in the present invention can be obtained by, for example, oxidizing 3-isocamphylcyclohexanol (i.e., a mixture of trans- and cis-isomers). The 3-isocamphylcyclohexanol is contained in an amount of about 20 to 40% by weight in substituents for sandalwood oil marketed under trade names of Santalex, etc. In the present invention, use can be made of 3-isocamphylcyclohexanone isolated and purified by high performance liquid chromatography, etc. Alternatively, it is possible to use a composition as such, which contains about 20 to 40% by weight of 3-isocamphylcyclohexanone and is obtained by oxidizing a marketed substitute for sandalwood oil such as Santalex.

The 3-isocamphylcyclohexanol or a marketed substitute for sandalwood oil such as Santalex may be oxidized in accordance with a method commonly employed for oxidizing secondary alcohols to obtain ketones. For example, the oxidation may be carried out in the presence of an oxidizing reagent or a dehydrogenation catalyst. Although chromates may be cited as the oxidizing reagent, the use of these compounds is restricted from the viewpoint of environmental pollution. It is therefore recommended to use a dehydrogenation catalyst therefor.

Examples of the dehydrogenation catalyst include those consisting of transition metal oxides as the main component. The transition metal oxides are exemplified by copper oxide (CuO), chromium oxide ($Cr_2O_3$), zinc oxide (ZnO), nickel oxide (NiO), etc. Either one of these compounds or a combination of two or more thereof may be employed as the catalyst. Furthermore, it may contain as a promoter a small amount of manganese oxide ($Mn_2O_3$), barium oxide (BaO), etc. Preferable examples of the catalyst include those composed of copper oxide and oxides of other transition metals such as copper-chromium catalyst (composed of copper oxide and chromium oxide), copper-zinc oxide (composed of copper oxide and zinc oxide) and copper-chromium-zinc catalyst (composed of copper oxide, chromium oxide and zinc oxide). These dehydrogenation catalysts may be produced by publicly known methods. Alternatively, commercially available ones may be used as such.

The dehydrogenation catalyst may be used in an amount about 1/5 to 1/100,000 times by weight, preferably 1/20 to 1/5,000 times by weight, as much as the 3-isocamphylcyclohexanol.

Although the oxidative reaction with the use of the dehydrogenation catalyst may be carried out in an appropriate solvent, it is preferable from an economical viewpoint to perform the reaction while using little solvent.

The oxidative reaction with the use of the dehydrogenation catalyst is carried out usually at a temperature of about 50° to 300° C., preferably at about 150° to 280° C. Although the reaction period varies depending on the reaction conditions employed (temperature, amount of the catalyst, etc.), the reaction is completed within about 1 to 20 hours.

The oxidative reaction may be carried out either in the atmosphere or under an inert gas atmosphere. Examples of the gas usable herein include nitrogen, argon, helium and carbon dioxide. Either one of these gases or a mixture of two or more thereof may be used for the reaction.

The oxidative reaction may be carried out under a pressure of from about 0.001 to 10 atm, preferably from about 0.01 to 0.5 atm.

The oxidative reaction with the use of the dehydrogenation catalyst may be also effected by vaporizing 3-isocamphylcyclohexanol and then bringing the gaseous substance into contact with a solid catalyst which has been heated.

The ruthenium/phosphine complex to be used as the catalyst in the hydrogenation reaction in the present invention is a compound having a phosphine compound, preferably an organic phosphine compound, coordinated with ruthenium. It may further have an auxiliary ligand. It may be either a mononuclear complex or a multinuclear complex.

As this complex, a commercially available one may be used as such. Alternatively, use can be made therefor of a complex prepared in situ in accordance with a publicly known method. In the latter case, for example, a ligand is added, in an amount of 1 to 4 equivalents to ruthenium, to a commercially available ruthenium salt or ruthenium complex. Alternatively, a ruthenium or a ruthenium complex and a ligand are separately added in the step of the hydrogenation of the present invention so as to form a complex in the reaction system. It is also possible to use a ligand in excess, a complex mixed with an additive such as triethylamine or a Lewis acid, or a complex which has been activated by reduction.

The organic phosphine compound to be coordinated with ruthenium may be either a monodentate ligand or a multidentate (i.e., bidentate or higher) one. Examples thereof include a monodentate ligand represented by the following formula (III):

PR$^1$R$^2$R$^3$   (III)

wherein R$^1$, R$^2$ and R$^3$ may be the same or different and each represents an optionally substituted alkyl group, an optionally substituted aralkyl group or an optionally substituted aryl group;
or a bidentate ligand represented by the following formula (IV):

R$^4$R$^5$P—A$^1$—PR$^6$R$^7$   (IV)

wherein R$^4$, R$^5$, R$^6$ and R$^7$ may be the same or different and each represents an optionally substituted alkyl group, an optionally substituted aralkyl group or an optionally substituted aryl group; and A$^1$ represents an optionally substituted alkylene group, —A$^2$—Ar—Ar—A$^2$— or —Ar—Ar—, wherein A$^2$ represents an optionally substituted alkylene group, and —Ar—Ar— represents a 1,1'-biphenyl group having a bond at the 2,2'-position, a 1,1'-binaphthyl group having a bond at the 2,2'-position, or a 5,5',6,6',7,7',8,8'-octahydro-1,1'-binaphthyl group having a bond at the 2,2'-position, wherein the biphenyl group may be substituted by a methyl, methoxy or dialkyl-substituted amino group and the binaphthyl group may be substituted by an alkali sulfonate.

The optionally substituted alkyl groups represented by R$^1$, R$^2$, R$^3$, R$^4$, R$^5$, R$^6$ and R$^7$ in the above formulae mean linear, branched or cyclic alkyl groups optionally having one or more substituents such as halogen atoms and alkoxy groups. Preferable examples thereof include linear or branched alkyl groups having from 1 to 10 carbon atoms and cyclic alkyl groups having from 3 to 8 carbon atoms, more particularly, methyl, ethyl, butyl, octyl and cyclohexyl groups.

The optionally substituted aralkyl groups represented by R$^1$, R$^2$, R$^3$, R$^4$, R$^5$, R$^6$ and R$^7$ in the above formulae mean alkyl groups substituted by an aryl group optionally having one or more substituents such as halogen atoms, alkyl groups and alkoxy groups. Preferable examples of the aryl group therein include optionally substituted phenyl and naphthyl groups. Preferable examples of the alkyl group in the aralkyl groups include those having 1 to 4 carbon atoms, more particularly, benzyl, phenethyl and naphthylmethyl groups.

The optionally substituted aryl groups represented by R$^1$, R$^2$, R$^3$, R$^4$, R$^5$, R$^6$ and R$^7$ in the above formulae mean aryl groups optionally having one or more substituents such as halogen atoms, alkyl groups and alkoxy groups. Preferable examples thereof include unsubstituted phenyl and naphthyl groups and phenyl and naphthyl groups substituted by a chlorine atom, a bromine atom, an iodine atom, a fluorine atom, linear or branched alkyl groups having from 1 to 4 carbon atoms or linear or branched alkoxy groups having from 1 to 4 carbon atoms. More preferable examples thereof include phenyl, naphthyl, p-chlorophenyl, p-bromophenyl, p-fluorophenyl, p-tolyl, p-t-butylphenyl, 3,5-dimethylphenyl and p-methoxyphenyl groups. Among all, phenyl and p-tolyl groups are particularly preferable therefor.

The optionally substituted alkylene groups represented by A$^1$ and A$^2$ mean linear or branched alkylene groups optionally having one or more substituents such as halogen atoms and alkoxy groups. Preferable examples thereof include unsubstituted, linear or branched alkylene groups having from 1 to 5 carbon atoms. More preferable examples of A$^1$ include ethylene [—(CH$_2$)$_2$—], propylene [—(CH$_2$)$_3$—], butylene [—(CH$_2$)$_4$—] and dimethylethylene [—CH(CH$_3$)CH(CH$_3$)—] groups, while a methylene group (—CH$_2$—) is particularly preferable as A$^2$.

Preferable examples of the ligand represented by the above formula (III) include trimethylphosphine, triethylphosphine, tributylphosphine, trioctylphosphine, tricyclohexylphosphine, tribenzylphosphine, triphenylphosphine, tri(p-chlorophenyl)phosphine, tri(p-bromophenyl)phosphine, tri(p-fluorophenyl)phosphine, tri(p-tolyl)phosphine, tri(p-t-butylphenyl)phosphine, tri(3,5-dimethylphenyl)phosphine, tri(p-methoxyphenyl)phosphine, methyldiphenylphosphine and dimethylphenylphosphine.

Among the ligands represented by the above formula (IV), preferable examples of those wherein A$^1$ is an optionally substituted alkylene group include 1,2-bis(dimethylphosphino)ethane, 1,3-bis(dimethylphosphino)propane, 1,4-bis(dimethylphosphino)butane, 1,2-bis(diphenylphosphino)ethane (hereinafter referred to as "DPPE"), 1,3-bis(diphenylphosphino)propane (hereinafter referred to as "DPPP"), 1,4-bis(diphenylphosphino)butane (hereinafter referred to as "DPPB"), 1,2-bis[di(p-tolyl)phosphino]ethane, 1,3-bis[di(p-tolyl)phosphino]propane, 1,4-bis[di(p-tolyl)phosphino]butane and 2,3-bis(diphenylphosphino)butane (hereinafter referred to as "CHIRAPHOS").

Among the ligands represented by the above formula (IV), preferable examples of those wherein A$^1$ is represented by "—A$^2$—Ar—Ar—A$^2$—" include 2,2'-bis(diphenylphosphinomethyl)-1,1'-biphenyl and 2,2'-bis(diphenylphosphinomethyl)-1,1'-binaphthyl.

Among the ligands represented by the above formula (IV), preferable examples of those wherein A$^1$ is represented by "—Ar—Ar—" include 2,2'-dimethyl-6,6'-bis(dicyclohexylphosphino)-1,1'-biphenyl (hereinafter referred to as "BICHEP"), 2,2'-dimethyl-6,6'-bis(diphenylphosphino)-1,1'-biphenyl (hereinafter referred to as "BIPHEMP"), 2,2'-dimethoxy-6,6'-bis(diphenylphosphino)-1,1'-biphenyl, 2,2',4,4'-tetramethoxy-6,6'-bis(diphenylphosphino)-1,1'-biphenyl, 2,2'-dimethyl-4,4'-bis(dimethylamino)-6,6'-bis(diphenylphosphino)-1,1'-biphenyl, 2,2'-bis(diphenylphosphino)-1,1'-binaphthyl (hereinafter referred to as "BINAP"), 2,2'-bis(di-p-tolylphosphino)-1,1'-binaphthyl (hereinafter referred to as "Tol-BINAP"), 2,2'-bis(di-m-tolylphosphino)-1,1'-binaphthyl (hereinafter referred to as "m-Tol-BINAP"), 2,2'-bis(di-p-t-butylphenylphosphino)-1,1'-binaphthyl (hereinafter referred to as "t-Bu-BINAP"), 2,2'-bis[di-(3,5-dimethylphenyl)phosphino]-1,1'-binaphthyl (hereinafter referred to as "DM-BINAP"), 2,2'-bis(di-p-methoxyphenylphosphino)-1,1'-binaphthyl (hereinafter referred to as "MeO-BINAP"), 2,2'-bis(di-p-chlorophenylphosphino)-1,1'-binaphthyl (hereinafter referred to as "Cl-BINAP"), 2,2'-bis(dicyclopentylphosphino)-1,1'-binaphthyl (hereinafter referred to as "CpBINAP"), 2,2'-bis(dicyclohexylphosphino)-1,1'-binaphthyl (hereinafter referred to as "CyBINAP") and 2,2'-bis(diphenylphosphino)-5,5',6,6',7,7',8,8'-octahydro-1,1'-binaphthyl (hereinafter referred to as "H$_8$-BINAP").

Among the ligands represented by the above formula (IV), CHIRAPHOS and those wherein A$^1$ is represented by —A$^2$—Ar—Ar—A$^2$— or —Ar—Ar— have asymmetric structures and occur as (S)-isomers, (R)-isomers or racemic modifications all of which fall within the scope of the present invention. Regarding these ligands with the asymmetric structures, the indication of (S)- or (R)- is not given herein except in the Examples.

It is particularly preferable in the present invention to use, from among the ligands as described above, those represented by the formula (III).

Examples of the auxiliary ligand which may be contained in the ruthenium/phosphine complex include 1,5-cyclooctadiene, benzene, p-cymene, acetonitrile, benzonitrile, pyridine, quinoline, isoquinoline, acetic acid and acetylacetonate.

Preferable examples of the ruthenium/phosphine complex are the complexes 1 to 4 represented by the following formulae (V) to (VIII).

Complex 1: $RuH_a(X^1)_bL_c$ (V)

wherein $X^1$ represents a halogen atom or a group represented by "$R^8COO$", wherein $R^8$ represents a hydrogen atom, an alkyl group having from 1 to 4 carbon atoms or a halogenated alkyl group having from 1 to 4 carbon atoms; L represents an organic phosphine compound; a and b are each an integer of from 0 to 2, provided that (a+b) is 2; when L is monodentate ligand, c is an integer of from 3 to 4; and when L is bidentate ligand, c is an integer of from 1 to 2.

Complex 2: $(RuH_dL_e)(X^2)_f$ (VI)

wherein $X^2$ represents $ClO_4$, $PF_6$ or $BF_4$; L is as defined above; when L is monodentate ligand, e is 2 and f is 2 when d is 0; and e is 4 and f is 1 when d is 1; and when L is bidentate ligand, e is 1 and f is 2 when d is 0; and e is 2 and f is 1 when d is 1.

Complex 3: $[(RuX^3)(Bz)L_h](X^4)_g$ (VII)

wherein $X^3$ represents a halogen atom; Bz represents optionally substituted benzene; $X^4$ represents a halogen atom, $ClO_4$, $PF_6$, $BF_4$ or $BPh_4$, wherein Ph represents a phenyl group, the same will apply hereinafter; L is as defined above; when L is monodentate ligand, h is 2 and g is 1 or g may be 3 when $X^3$ and $X^4$ are each an iodine atom; and when L is bidentate ligand, h is 1 and g is 1 or g may be 3 when $X^3$ and $X^4$ are each an iodine atom.

Complex 4: $(Ru_2Cl_4L_w)(T)$ (VIII)

wherein T represents a tertiary amine; and L is as defined above; when L is monodentate ligand, w is 4; and when L is bidentate ligand, w is 2.

In the above formulae, the organic phosphine compounds represented by L are those selected from among the organic phosphine compounds as described above.

Preferable examples of $X^1$ in the formula (V) include a chlorine atom, a bromine atom, an iodine atom, HCOO, $CH_3COO$ and $CF_3COO$. Among all, a chlorine atom is preferable therefor.

In the above formula (V), there are 3 combinations of a with b, namely, (a=0; b=2), (a=1; b=1) and (a=2; b=0). Among them, the combination of (a=0; b=2) is a preferable one. When $X^1$ is a halogen atom, then it is particularly preferable that c is 3 or 4.

Examples of the halogen atoms represented by $X^3$ and $X^4$ in the above formula (VII) include chlorine, bromine and iodine atoms.

The optionally substituted benzene represented by Bz in the above formula (VII) means a benzene ring optionally having one or more substituents such as alkyl groups, alkoxy groups, alkoxycarbonyl groups and halogen atoms. Preferable examples thereof include unsubstituted benzene and benzene substituted by alkyl groups having from 1 to 4 carbon atoms, alkoxy groups having from 1 to 4 carbon atoms, alkoxycarbonyl groups having from 1 to 4 carbon atoms, a chlorine atom, a bromine atom or an iodine atom. More particularly, citation may be made therefor of benzene, toluene, xylene, trimethylbenzene, hexamethylbenzene, ethylbenzene, t-butylbenzene, p-cymene, cumene, anisole, methyl benzoate, chlrobenzene, etc.

Examples of the tertiary amine represented by T in the above formula (VIII) include triethylamine, tributylamine, ethyldiisopropylamine, 1,8-bis(dimethylamino)naphthalene, dimethylaniline, pyridine and N-methylpyridine. Among all, triethylamine is preferable therefor.

Preferable examples of the complex 1 are as follows.
$RuH_2(PPh_3)_4$,
$RuHCl(PPh_3)_4$,
$RuH(HCOO)(PPh_3)_3$,
$RuH(CH_3COO)(PPh_3)_3$,
$RuCl_2(PPh_3)_3$,
$RuCl_2(PPh_3)_4$,
$RuBr_2(PPh_3)_4$,
$RuI_2(PPh_3)_4$,
$RUCl_2[P(CH_3)Ph_2]_4$,
$RUCl_2[P(CH_3)_2Ph]_4$,
$RuCl_2[P(CH_3)_3]_4$,
$RuCl_2[Ph_2P-(CH_2)_2-PPh_2]_2$,
$RUCl_2(CHIRAPHOS)_2$,
$RuCl_2(BINAP)$,
$Ru(CH_3COO)_2(Tol-BINAP)$ and
$Ru(CF_3COO)_2(Tol-BINAP)$.

Preferable examples of the complex 2 are as follows.
$[Ru(BINAP)](ClO_4)_2$,
$[(Ru(m-Tol-BINAP)](PF_6)_2$,
$[Ru(MeO-BINAP)](BF_4)_2$,
$[RuH(BIPHEMP)_2]ClO_4$ and
$[RuH(t-Bu-BINAP)_2]PPF_6$.

Preferable examples of the complex 3 are as follows.
$[RuCl(benzene)(BINAP)]Cl$,
$[RuCl(p-cymene)(DPPE)]Cl$,
$[RuCl(p-cymene)(DPPP)]Cl$,
$[RuCl(p-cymene)(DPPB)]Cl$,
$[RuI(benzene)(Tol-BINAP)]Cl$,
$[RuI(p-cymene)(Tol-BINAP)]I$ and
$[RuI(p-cymene)(BINAP)]I_3$.

Preferable examples of the complex 4 are as follows wherein Et represents an ethyl group.
$[Ru_2Cl_4(BINAP)_2](NEt_3)$,
$[RU_2Cl_4(DM-BINAP)_2]$ $(NEt_3)$ and
$[Ru_2Cl_4(H_8-BINAP)_2]$ $(NEt_3)$.

Among the complexes as described above, the complexes 1 are preferably employed in the present invention from the viewpoint of the reaction selectivity, etc.

It is known that many of the above-mentioned complexes are usable as catalysts in reactions wherein ketones are hydrogenated to thereby give alcohols. However, it has never been known so far that these complexes are usable for stereoselectively hydrogenating 3-isocamphylcyclohexanone to thereby give trans-3-isocamphylcyclohexanol with a high purity. It is reported, for example, that a mixture of 2-cyclohexenol with cyclohexanol (70:30) can be obtained by hydrogenating 2-cyclohexenone with the use of $RuCl_2(PPh_3)_3$ as a catalyst

[T. Ohkuma et al., *J. Am. Chem. Soc.*, vol. 117, pp. 10417–10418 (1995)]. However, it has never been suggested that when cis- and trans-isomers are formed by the hydrogenation into an alcohol, a specific isomer can be selectively obtained, as is in the case of the present invention.

The base containing an alkali metal or an alkaline earth metal to be used in the present invention is a compound represented by, for example, the following general formula (IX):

$$M(R^9) \qquad (IX)$$

wherein M represents an alkali metal or an alkaline earth metal; and $R^9$ represents a hydroxyl group, an alkoxy group having from 1 to 4 carbon atoms or a mercapto group. The bases containing alkali metals are preferable therefor. Preferable examples of the base include KOH, $Ca(OH)_2$, KOMe, KOtBu, LiOH, LiOMe, LiOtBu, NaOH and NaOMe wherein Me represents a methyl group and tBu represents a t-butyl group. Among all, those containing alkali metals are preferable and KOH and NaOH are particularly preferable therefor.

In the present invention, the above-mentioned base is employed in an amount of from about 0.5 to 100 equivalents, preferably from about 1 to 40 equivalents to the complex.

Examples of the amine to be used in the present invention are primary, secondary or tertiary amines represented by the following general formula (X):

$$NR^{10}R^{11}R^{12} \qquad (X)$$

wherein $R^{10}$, $R^{11}$ and $R^{12}$ are the same or different and each represents a hydrogen atom, an optionally substituted alkyl group, an optionally substituted aralkyl group or an optionally substituted aryl group, provided that $R^{10}$, $R^{11}$ and $R^{12}$ do not represent hydrogen atoms at the same time; primary, secondary or tertiary diamines represented by the following general formula (XI):

$$NR^{13}R^{14}-Z-NR^{15}R^{16} \qquad (XI)$$

wherein $R^{13}$, $R^{14}$, $R^{15}$ and $R^{16}$ are the same or different and each represents a hydrogen atom, an optionally substituted alkyl group, an optionally substituted aralkyl group or an optionally substituted aryl group; and Z represents an optionally substituted, saturated or unsaturated carbon chain having from 1 to 6 carbon atoms or an optionally substituted, saturated or unsaturated carbon ring having from 3 to 6 carbon atoms; and other cyclic amines.

The optionally substituted alkyl groups represented by $R^{10}$, $R^{11}$, $R^{12}$, $R^{13}$, $R^{14}$, $R^{15}$ and $R^{16}$ in the above formulae mean linear, branched or cyclic alkyl groups optionally having one or more substituents such as alkoxy groups. Preferable examples thereof include linear or branched alkyl groups having from 1 to 10 carbon atoms and cyclic alkyl groups having from 5 to 8 carbon atoms.

The optionally substituted aralkyl groups represented by $R^{10}$, $R^{11}$, $R^{12}$, $R^{13}$, $R^{14}$, $R^{15}$ and $R^{16}$ in the above formulae mean alkyl groups substituted by an aryl group optionally having one or more substituents such as alkyl and alkoxy groups. As the aryl group therein, a phenyl group is preferable. As the alkyl group in the aralkyl groups, those having 1 to 4 carbon atoms are preferable. More particularly, a benzyl group is preferable therefor.

The optionally substituted aryl groups represented by $R^{10}$, $R^{11}$, $R^{12}$, $R^{13}$, $R^{14}$, $R^{15}$ and $R^{16}$ in the above formulae mean aryl groups optionally having one or more substituents such as alkyl and alkoxy groups. Preferable examples thereof include unsubstituted phenyl and naphthyl groups and phenyl or napthyl groups substituted by linear or branched alkyl groups having from 1 to 4 carbon atoms or linear or branched alkoxy groups having from 1 to 4 carbon atoms.

Particular examples of the amine to be used in the present invention include monoamines such as methylamine, ethylamine, propylamine, isopropylamine, butylamine, isobutylamine, t-butylamine, hexylamine, octylamine, dodecylamine, cyclopentylamine, cyclohexylamine, benzylamine, dimethylamine, diethylamine, dipropylamine, diisopropylamine, dibutylamine, diisobutylamine, di-t-butylamine, dihexylamine, dicyclopentylamine, dicyclohexylamine, dibenzylamine, trimethylamine, triethylamine, tripropylamine, ethyldiisopropylamine, tributylamine, trihexylamine, tribenzylamine, benzyldimethylamine, aniline, p-toluidine, N,N-dimethylaniline, diphenylamine, triphenylamine, piperidine, piperazine, morpholine, N-methylpiperidine, N-methyhlpiperazine and N-methyhlmorpholine; diamines such as ethylenediamine, trimethylenediamine, tetramethylenediamine, pentamethylenediamine, hexamethylenediamine, N-methylethylenediamine, N,N'-dimethylethylenediamine, N,N'-dimethylpropylenediamine, N,N'-dimethyltetramethylenediamine, N,N'-diethylethylenediamine, N,N'-diethylpropylenediamine, N,N'-diethyltetramethylenediamine, N,N'-dibenzylethylenediamine, N,N'-dibenzylpropylenediamine, N,N'-dibenzyltetramethylenediamine, N,N'-diphenylethylenediamine, N,N'-diphenylpropylenediamine, N,N'-diphenyltetramethylenediamine, N,N,N'-trimethylethylenediamine, tetramethylethylenediamine, tetramethylpropylenediamine, tetramethyltetramethylenediamine, tetraethylethylenediamine, tetraethylpropylenediamine, tetraethyltetramethylenediamine, tetrabenzylethylenediamine, tetrabenzylpropylenediamine, tetrabenzyltetramethylenediamine, tetraphenylethylenediamine, tetraphenylpropylenediamine, tetraphenyltetramethylenediamine and o-phenylenediamine; and optically active diamines such as optically active 1,2-diphenylethylenediamine, 1,3-diphenylpropylenediamine, 1,4-diphenyltetramethylenediamine, 1,2-diaminopropane, 1,1-diphenyl-1,2-diaminopropane, 1,1-di(p-methoxyphenyl)-1,2-diaminopropane, 2,3-diaminobutane, 2,4-diaminopentane, 2,5-diaminohexane, 1,2-diaminocyclopentane and 1,2-diaminocyclohexane.

Among the amines as cited above, it is preferable in the present invention to use the diamines represented by the formula (XI), still preferably primary diamines wherein $R^{13}$, $R^{14}$, $R^{15}$ and $R^{16}$ in the formula (XI) are each a hydrogen atom and Z is a saturated carbon chain having from 1 to 4 carbon atoms. Particular examples thereof include ethylenediamine, trimethylenediamine and tetramethylenediamine.

In the present invention, the amine is employed in an amount of from about 1 to 8 equivalents, preferably from about 2 to 4 equivalents, to the complex (in the case of a monoamine), or from about 0.5 to 4 equivalents, preferably from about 1 to 4 equivalents, to the complex (in the case of a diamine).

The production process of the present invention is performed by hydrogenating 3-isocamphylcyclohexanone with the use of such a ruthenium/phosphine complex as described above as a catalyst in the presence of a base and an amine in a hydrogen gas stream atmosphere. It is recommended that the molar ratio of the reaction substrate (i.e., 3-isocamphylcyclohexanone) to the catalyst ranges from about 1/5 to 1/100,000 [substrate/catalyst (S/C) molar ratio=5 to 100,000], preferably from about 1/200 to 1/50,000 (S/C=200 to 50,000). It is preferable to carry out the reaction under stirring. When the catalyst is used in a small amount, in particular, it is preferable to carry out the reaction under 20 mechanically stirring with a mechanical stirrer, etc.

The reaction temperature ranges usually from about −30° to 250° C., preferably from about 15° to 100° C. Although the reaction time varies depending on various conditions such as the concentration of the reaction substrate employed, the amount of the catalyst, temperature and hydrogen gas pressure, the reaction is completed within about several minutes to 30 hours. The completion of the reaction can be confirmed by gas chromatography, etc.

The hydrogen gas pressure ranges from about 1 to 200 atm, preferably from about 3 to 100 atm. Hydrogen may be diluted with other gas(es) which are inert in the reaction. For example, hydrogen may be diluted with methane, nitrogen, argon, helium, carbon dioxide or mixtures thereof.

The reaction of the present invention can be performed substantially by using the substrate alone, i.e., without any solvent. Alternatively, an appropriate solvent may be employed therefor. The solvent, if employed, may be an arbitrary one without restriction, so long as it exerts no undesirable effect on the reaction. For example, use can be made of a solvent, either alone or as a mixture thereof, selected from among water; hydrocarbons such as hexane, heptane, octane, nonane, decane, benzene, toluene and xylene; ethers such as tetrahydrofuran, dioxane, dimethoxyethane, diisopropyl ether and diethylene glycol dimethyl ether; esters such as ethyl acetate, butyl acetate, ethyl propionate and ethyl acetoacetate; alcohols such as methanol, ethanol, n-propanol and isopropanol; nitriles such as acetonitrile; phosphorous acid and its esters such as trimethyl phosphite, dimethyl phosphite, monomethyl phosphite, triethyl phosphite, tributyl phosphite, trioctyl phosphite, triphenyl phosphite, dimethylphenyl phosphite and methyldiphenyl phosphite; sulfoxides such as dimethyl sulfoxide, diethyl sulfoxide, dibenzyl slfoxide, diphenyl sulfoxide and tetramethylene sulfoxide; and amides such as formamide, N,N-dimethylformamide, N,N-dimethylacetamide and N-methylpyrrolidone. Among all, it is preferable to use alcohols such as methanol, ethanol and isopropanol therefor and isopropanol is the most desirable one.

In the present invention, the ratio of the solvent, if employed, to the reaction substrate is not particularly restricted. It is preferable to add the solvent in an amount about 0.5 to 100 times by weight as much as the substrate.

After the completion of the reaction, purification is effected by filtration, concentration under reduced pressure, distillation, etc. in accordance with the conventional manner. Thus highly pure trans-3-isocamphylcyclohexanol containing about 70% by weight or more of the trans-isomer can be obtained. The trans-3-isocamphylcyclohexanol thus obtained is in the form of a mixture of (1S,3S)-isocamphylcyclohexanol with (1R,3R)-isocamphylcyclohexanol. Since these components are both essentially required in the expression of the sandalwood oil-like fragrance, the mixture can be advantageously used as a perfume ingredient as such. Needless to say, it is also possible to separate (1S,3S)-isocamphylcyclohexanol from (1R,3R)-isocamphylcyclohexanol by, for example, high performance liquid chromatography before using.

When a composition which contains about 20 to 40% by weight of 3-isocamphylcyclohexanone and obtained by oxidizing a marketed substitute for sandalwood oil (for example, Santalex) is employed as the reaction substrate in the process of the present invention, it is possible to obtain a composition containing about 15 to 35% by weight of trans-3-isocamphylcyclohexanol depending on the content thereof in the starting material. That is to say, the process of the present invention makes it possible to largely elevate the content of trans-3-isocamphylcyclohexanol, which is essentially required in the expression of the sandalwood oil-like fragrance, in a marketed sandalwood oil substitute containing trans-3-isocamphylcyclohexanol in an amount of about 8% by weight at the largest. As a result, the fragrance is strengthened and, furthermore, the fragrance qualities can be improved, since the by-products are reduced. According to the process of the present invention, namely, the fragrance of a marketed substitute for sandalwood oil can be considerably improved.

According to the process of the present invention, trans-3-isocamphylcyclohexanol having a high purity can be obtained while using an inexpensive catalyst in a small amount. Owing to these characteristics, the process of the present invention is very advantageous from an economical viewpoint and suitable for industrial production. The trans-3-isocamphylcyclohexanol thus obtained, which is known as a component essentially required in the expression of the sandalwood oil-like fragrance, has a fragrance highly excellent in both of qualities and strength. Thus this product is useful as a perfume ingredient.

To further illustrate the present invention in greater detail, and not by way of limitation, the following Examples will be given. In these Examples, analytical data were obtained by using the instruments and conditions as will be specified below.

High performance liquid chromatography:
pump: LC-6A (manufactured by Shimadzu Corporation)
column: Unisil-Q 30-5 (10.7 mm×250 mm) (manufactured by GL Sciences Inc.)
detector: differential refractometric detector Model LRD-771 (manufactured by Laboratory System).
Gas chromatography:
instrument: HP-5890 (manufactured by Hewlett-Packaed, Co.)
column: HP-20M fused silica capillary column (0.20 mm×25 m) (manufactured by Hewlett-Packaed, Co.)
measuring temperature: 55°–215° C. (program rate 4° C./min)
injection temperature: 250° C.
carrier gas: helium (0.6 ml/min)
internal standard: isopropyl myristate.
Gas chromatography (GC/MS):
instrument: HP-5890 Series II (manufactured by Hewlett-Packaed, Co.) and M-2000A (manufactured by Hitachi, Ltd.)
column: BC-WAX (0.25 mm×50 m, 0.15 µm) (manufactured by GL Sciences Inc.)
measuring temperature: 70°–220° C. (program rate 4° C./min)
injection temperature: 250° C.
Proton magnetic resonance spectrometry ($^1$H-NMR):
instrument: Model AMX-400 (400 MHz), FT-NMR spectrometer (manufactured by Bruker JAPAN Co., Ltd.)
internal standard substance: tetramethylsilane.
$^{13}$C magnetic resonance spectrometry ($^{13}$C-NMR):
instrument: Model AMX-400 (100 MHz) (manufactured by Bruker JAPAN Co., Ltd.).

Infrared spectrometry (IR):
instrument: FTIR-8200 PC (manufactured by Shimadzu Corporation)
method: film method.

Melting point:
instrument: Yanagimoto melting point microanalyzer MP-S2 (manufactured by Yanagimoto Seisakusho).

The melting points given in the following Examples are uncorrected data.

EXAMPLE 1

Into a stainless autoclave (100 ml) were fed, under a nitrogen atmosphere, 4.0 g (17.1 mmol) of 3-isocamphylcyclohexanone, 32.8 mg (0.034 mmol) of $RuCl_2(PPh_3)_3$, 1.72 ml (0.069 mmol) of a 0.04M solution of KOH in isopropanol, 3.76 ml (0.034 mmol) of a 0.009M solution of trimethylenediamine in isopropanol and 10 ml of isopropanol.

The mixture was stirred under a hydrogen gas pressure of 10 atm at room temperature for 2.5 hours. When the reaction mixture was analyzed by gas chromatography, it was found out that trans-3-isocamphylcyclohexanol was thus formed at a conversion ratio of 100% and at a selectivity of 84% d.e. (trans:cis=92:8; by weight). The reaction mixture was filtered and the filtrate was concentrated under reduced pressure. Then the oily substance thus obtained was distilled by using a Kugel-Rohr distillation apparatus at 170° C./20 mmHg to thereby give 3.15 g of the target trans-3-isocamphylcyclohexanol (yield:78%).

The trans-3-isocamphylcyclohexanol thus obtained was further separated into (1S,3S)-isocamphylcyclohexanol and (1R,3R)-isocamphylcyclohexanol by high performance liquid chromatography [eluent: hexane/ethyl acetate (7/1); flow rate: 5 ml/min]. Component 1: retention time=16.6 minutes. Component 2: retention time=18.0 minutes. The ratio of the component 1 to the component 2: 1/1. It was not identified which was the (1S,3S)-isomer or the (1R,3R)-isomer. The physical data of each component were determined.

Component 1:

m.p.: 91°–94° C.

MS(EI)(m/z): 95 (100), 81 (52), 135 (43), 110 (33), 236 (4).

$^1$H-NMR (CDCl$_3$) δ ppm: 4.06 (1H, brs), 1.87–0.65 (18H, m), 0.90 (3H, s), 0.84 (3H, s), 0.82 (3H, d, J=7.4 Hz).

$^{13}$C-NMR (CDCl$_3$) δ ppm: 66.8, 49.4, 48.9, 48.0, 47.9, 40.4, 38.8, 36.3, 33.4, 33.4, 31.1, 29.4, 27.4, 24.8, 20.0, 16.2.

IR (film) (cm$^{-1}$): 3420, 2900, 1450, 1385, 1140, 1030, 1020.

Component 2:

m.p. : 92°–93° C.

MS(EI)(m/z): 97 (100), 135 (94), 81 (72), 123 (42), 236 (4).

$^1$H-NMR (CDCl$_3$) δ ppm: 4.06 (1H, brs), 1.87–0.65 (18H, m), 0.91 (3H, s), 0.84 (3H, s), 0.83 (3H, d, J=7.5 Hz).

$^{13}$C-NMR (CDCl$_3$) δ ppm: 66.8, 49.5, 49.0, 48.0, 48.0, 39.2, 37.0, 36.4, 33.3, 33.0, 31.4, 27.4, 24.8, 20.0, 16.2.

IR (film) (cm$^{-1}$): 3400, 2900, 1450, 1385, 1140, 1030, 1020.

EXAMPLES 2 TO 22

Hydrogenation was carried out by the same method as the one described in Example 1 but varying the reaction conditions. The results are given in the following Tables 1 to 4.

TABLE 1

| Ex. No. | Catalyst*$^1$ | S/C*$^2$ | Solvent | SO/S*$^3$ | Base | B/C*$^4$ | Amine |
|---|---|---|---|---|---|---|---|
| 2 | RuCl$_2$(PPh$_3$)$_3$ | 200 | isopropanol | 3 | KOH | 30 | trimethylenediamine |
| 3 | RuCl$_2$(PPh$_3$)$_3$ | 200 | isopropanol | 3 | KOH | 30 | trimethylenediamine |
| 4 | RuCl$_2$(PPh$_3$)$_3$ | 500 | isopropanol | 3 | KOH | 1 | trimethylenediamine |
| 5 | RuCl$_2$(PPh$_3$)$_3$ | 500 | isopropanol | 2.4 | KOH | 2 | trimethylenediamine |
| 6 | RuCl$_2$(PPh$_3$)$_3$ | 500 | isopropanol | 3 | KOH | 5 | trimethylenediamine |
| 7 | RuCl$_2$(PPh$_3$)$_3$ | 500 | isopropanol | 3 | KOH | 10 | trimethylenediamine |
| 8 | RuCl$_2$(PPh$_3$)$_3$ | 500 | isopropanol | 3.4 | KOH | 30 | trimethylenediamine |
| 9 | RuCl$_2$(PPh$_3$)$_3$ | 500 | isopropanol | 3 | KOtBu | 2 | trimethylenediamine |
| 10 | RuCl$_2$(PPh$_3$)$_3$ | 500 | isopropanol | 3 | NaOMe | 2 | trimethylenediamine |
| 11 | RuCl$_2$(PPh$_3$)$_3$ | 500 | isopropanol | 3 | KOH | 2 | trimethylenediamine |
| 12 | RuCl$_2$(PPh$_3$)$_3$ | 500 | isopropanol | 3 | KOH | 2 | trimethylenediamine |
| 13 | [RuCl(p-cymene)-(DPPE)]Cl | 500 | isopropanol | 3 | koH | 2 | trimethylenediamine |
| 14 | {Ru$_2$Cl$_4$[(S)-BINAP]$_2$}(NEt$_3$) | 500 | isopropanol | 3 | KOH | 2 | trimethylenediamine |
| 15 | {Ru$_2$Cl$_4$[(S)-(H$_8$-BINAP)]$_2$}(NEt$_3$) | 500 | isopropanol | 3 | KOH | 2 | trimethylenediamine |
| 16 | RuCl$_2$(PPh$_3$)$_3$ | 1000 | isopropanol | 3 | KOH | 2 | trimethylenediamine |
| 17 | RuCl$_2$(PPh$_3$)$_3$ | 1000 | isopropanol | 3 | KOH | 4 | trimethylenediamine |
| 18 | RuCl$_2$(PPh$_3$)$_3$ | 2000 | isopropanol | 3 | KOH | 30 | trimethylenediamine |
| 19 | RuCl$_2$(PPh$_3$)$_3$ | 3000 | isopropanol | 3 | KOH | 30 | trimethylenediamine |

TABLE 2

| Ex. No. | Catalyst*1 | A/C*5 | Hydrogen pressure (atm) | Reaction temp. (°C.) | Reaction time (hr) | Conversion rate (%) | Trans:cis weight ratio |
|---|---|---|---|---|---|---|---|
| 2 | RuCl₂(PPh₃)₃ | 1 | 10 | room temp. | 5 | 100 | 87:13 |
| 3 | RuCl₂(PPh₃)₃ | 1 | 10 | room temp. | 5 | 91 | 87:13 |
| 4 | RuCl₂(PPh₃)₃ | 1 | 10 | room temp. | 21 | 100 | 86:14 |
| 5 | RuCl₂(PPh₃)₃ | 1 | 50 | room temp. | 21 | 100 | 86:14 |
| 6 | RuCl₂(PPh₃)₃ | 1 | 50 | room temp. | 5 | 97 | 87:13 |
| 7 | RuCl₂(PPh₃)₃ | 1 | 50 | room temp. | 5 | 97 | 89:11 |
| 8 | RuCl₂(PPh₃)₃ | 1 | 50 | room temp. | 5 | 96 | 89:11 |
| 9 | RuCl₂(PPh₃)₃ | 1 | 50 | room temp. | 5 | 68 | 87:13 |
| 10 | RuCl₂(PPh₃)₃ | 1 | 50 | room temp. | 5 | 60 | 88:12 |
| 11 | RuCl₂(PPh₃)₃ | 4 | 50 | room temp. | 5 | 90 | 90:10 |
| 12 | RuCl₂(PPh₃)₃ | 1 | 50 | 50 | 5 | 65 | 89:11 |
| 13 | [RuCl(p-cymene)(DPPE)]Cl | 1 | 50 | room temp. | 5 | 70 | 75:25 |
| 14 | {Ru₂Cl₄[(S)-BINAP]₂}(NEt₃) | 1 | 50 | room temp. | 5 | 92 | 81:19 |
| 15 | {Ru₂Cl₄[(S)-(H₈-BINAP)]₂}(NEt₃) | 1 | 50 | room temp. | 5 | 92 | 85:15 |
| 16 | RuCl₂(PPh₃)₃ | 1 | 10 | room temp. | 5 | 90 | 85:15 |
| 17 | RuCl₂(PPh₃)₃ | 2 | 50 | room temp. | 5 | 97 | 91:9 |
| 18 | RuCl₂(PPh₃)₃ | 2 | 50 | room temp. | 5 | 97 | 90:10 |
| 19 | RuCl₂(PPh₃)₃ | 2 | 50 | room temp. | 5 | 97 | 90:10 |

TABLE 3

| Ex. No. | Catalyst*1 | S/C*2 | Solvent | SO/S*3 | Base | B/C*4 | Amine |
|---|---|---|---|---|---|---|---|
| 20 | RuCl₂(PPh₃)₃ | 5000 | isopropanol | 3 | KOH | 30 | trimethylenediamine |
| 21 | RuCl₂(PPh₃)₃ (in situ) | 1000 | isopropanol | 3 | KOH | 30 | trimethylenediamine |
| 22 | RuCl₂(PPh₃)₃ (in situ) | 3000 | isopropanol | 3 | KOH | 30 | trimethylenediamine |

Note
*1 in situ: Ruthenium chloride and the ligand were separately added to the hydrogenation reactor and then the complex was formed in the reaction mixture.
*2 Molar ratio of substrate (S) (3-isocamphylcyclohexanone)/catalyst (C).
*3 Weight ratio of solvent (SO)/catalyst (C).
*4 Molar ratio of base (B)/catalyst (C).
*5 Molar ratio of amine (A)/catalyst (C).

TABLE 4

| Ex. No. | Catalyst*1 | A/C*5 | Hydrogen pressure (atm) | Reaction temp. (°C.) | Reaction time (hr) | Conversion rate (%) | Trans:cis weight ratio |
|---|---|---|---|---|---|---|---|
| 20 | RuCl₂(PPh₃)₃ | 2 | 50 | room temp. | 5 | 89 | 90:10 |
| 21 | RuCl₂(PPh₃)₃ (in situ) | 4 | 50 | room temp. | 18 | 98 | 80:20 |
| 22 | RuCl₂(PPh₃)₃ (in situ) | 2 | 50 | room temp. | 5 | 97 | 90:10 |

Note
*1 in situ: Ruthenium chloride and the ligand were separately added to the hydrogenation reactor and then the complex was formed in the reaction mixture.
*2 Molar ratio of substrate (S) (3-isocamphylcyclohexanone)/catalyst (C).
*3 Weight ratio of solvent (SO)/catalyst (C).
*4 Molar ratio of base (B)/catalyst (C).
*5 Molar ratio of amine (A)/catalyst (C).

Referential Example: Production of 3-isocamphylcyclohexanone-containing composition via the oxidation of Santalex Into a four-necked flask provided with a vacuum stirrer and a Claisen's distillation apparatus were fed 152.0 g of Santalex (a composition containing 8% by weight of trans-3-isocamphylcyclohexanol and 14% by weight of cis-3-isocamphylcyclohexanol) and 3.04 g of a copper/chromium catalyst (N-203S, manufactured by JGC Corporation, composition: $CuO \cdot Cr_2O_3 \cdot MnO_2O_3$). The mixture was stirred under reduced pressure (90 mmHg, about 0.12 atm) at 220° C. and then the pressure was adjusted to 60 mmHg (about 0.08 atm). After reacting at 220° C. for 5 hours while monitoring the bubbling, the pressure was further reduced as such and the reaction mixture was purified by distillation (181° C./12 mmHg) to thereby give 141.5 g of a composition containing 22% by weight of 3-isocamphylcyclohexanone (yield: 94%).

The 3-isocamphylcyclohexanone thus obtained was further separated into (R)-isocamphylcyclohexanone and (S)-isocamphylcyclohexanone by high performance liquid chromatography [eluent: hexane/ethyl acetate (14/1); flow rate: 5 ml/min]. Component 1: retention time=12.2 minutes. Component 2: retention time=13.1 minutes. It was not identified which was the (R)-isomer or the (S)-isomer. The physical data of each component were determined.

Component 1:

MS(EI)(m/z): 97 (100), 81 (45), 137 (40), 69 (36), 234 (20).

$^1$H-NMR (CDCl$_3$) δ ppm: 2.53 (1H, m), 2.33–2.25 (2H, m), 2.04–1.81 (5H, m), 1.62–1.35 (4H, m), 1.27–0.92 (5H, m), 0.92 (3H, s), 0.85 (3H, s), 0.83 (3H, d, J=6.9 Hz).

$^{13}$C-NMR (CDCl$_3$) δ ppm: 212.1, 49.3, 48.8, 48.7, 47.8, 47.7, 44.0, 41.5, 39.2, 32.9, 31.2, 28.8, 27.4, 25.2, 24.7, 16.1.

IR (film) (cm$^{-1}$): 2950, 2870, 1720, 1480, 1450, 1320, 1220.

Component 2:

MS(EI)(m/z): 97 (100), 137 (52), 81 (38), 69 (30), 234 (15).

$^1$H-NMR (CDCl$_3$) δ ppm: 2.42 (1H, m), 2.36–2.20 (2H, m), 2.10–1.75 (5H, m), 1.62–1.30 (4H, m), 1.30–1.10 (5H, m), 0.92 (3H, s), 0.85 (3H, s), 0.84 (3H, d, J=7.2 Hz).

$^{13}$C-NMR (CDCl$_3$) δ ppm: 212.3, 49.3, 48.9, 48.5, 48.4, 45.9, 44.2, 41.5, 39.2, 33.0, 30.7, 30.6, 27.4, 25.2, 24.7, 16.1.

IR (film) (cm$^{-1}$): 2950, 2870, 1720, 1480, 1320, 1220.

EXAMPLE 23

Into a stainless autoclave (500 ml) were fed, under a nitrogen atmosphere, 46.88 g of the composition containing 3-isocamphylcyclohexanone obtained in Referential Example, 385.7 mg (0.4 mmol) of RuCl$_2$(PPh$_3$)$_3$, 20 ml (0.8 mmol) of a 0.04M solution of KOH in isopropanol, 40.0 ml (0.4 mmol) of a 0.01M solution of trimethylenediamine in isopropanol and 80 ml of isopropanol. The mixture was stirred under a hydrogen gas pressure of 50 atm at room temperature for 21 hours. Then the reaction mixture was concentrated. When the oily product thus obtained was analyzed by gas chromatography, it was found out that trans-3-isocamphylcyclohexanol was formed at a conversion ratio of 100% and at a selectivity of 72% d.e. (trans:cis= 86:14 by weight).

Next, the oily product was distilled with the use of a Claisen's distillation apparatus at 131° to 133° C./0.25 mmHg to thereby give 37.25 g of a composition containing 19% by weight of the target trans-3-isocamphylcyclohexanol (yield:80%).

Comparative Examples

In the following Examples, 3-isocamphylcyclohexanone was hydrogenated by using solid catalysts which had been publicly known prior to the present invention. It is obvious that, compared with the catalysts employed in the present invention, each of these known catalysts costs high and is inferior in the selectivity for the target trans-3-isocamphylcyclohexanol or fails to effect the reaction.

Comparative Example 1

2.34 g (10 mmol) of 3-isocamphylcyclohexanone was dissolved in 10 ml-of acetic acid and 59 mg of Adams' platinum catalyst was added thereto. Then the resulting mixture was stirred in a hydrogen gas stream at ordinary temperatures under atmospheric pressure for 4 hours. The reaction mixture was concentrated and the oily substance thus obtained was analyzed by gas chromatography. Thus, it was found out that 3-isocamphylcyclohexanol (trans:cis= 64:36 by weight) was formed at a conversion ratio of 93.0%.

Comparative Example 2

2.34 g (10 mmol) of 3-isocamphylcyclohexanone was dissolved in 10 ml of acetic acid and 117 mg of 5% palladium/carbon catalyst was added thereto. Then the resulting mixture was stirred in an autoclave under a hydrogen gas pressure of 50 atm at room temperature for 23 hours. The reaction mixture was filtered and the filtrate was concentrated. Then the oily substance thus obtained was analyzed by gas chromatography. Thus, it was found out that the reaction did not proceed at all and, therefore, nothing but the starting 3-isocamphylcyclohexanone could be recovered.

Comparative Example 3

1.52 g (6.5 mmol) of 3-isocamphylcyclohexanone was dissolved in 25 ml of isopropanol and 50 mg of 5% rhodium/carbon catalyst was added thereto. Then the resulting mixture was stirred in a hydrogen gas stream at ordinary temperatures under atmospheric pressure for 4 hours. The reaction mixture was filtered and the filtrate was concentrated. Then the oily substance thus obtained was analyzed by gas chromatography. Thus, it was found out that the reaction did not proceed at all and, therefore, nothing but the starting 3-isocamphylcyclohexanone could be recovered.

While the invention has been described in detail and with reference to specific embodiments thereof, it will be apparent to one skilled in the art that various changes and modifications can be made therein without departing from the spirit and scope thereof.

What is claimed is:

1. A process for producing trans-3-isocamphylcyclohexanol which comprises hydrogenating 3-isocamphylcyclohexanone represented by the following formula (I):

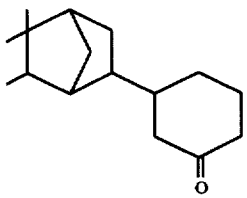

by using a ruthenium/phosphine complex as a catalyst in the presence of a base containing an alkali metal or an alkaline earth metal and an amine.

2. The process for producing trans-3-isocamphylcyclohexanol as claimed in claim 1, wherein the ruthenium/phosphine complex is an organic phosphine compound coordinated with ruthenium.

3. The process for producing trans-3-isocamphylcyclohexanol as claimed in claim 2, wherein the organic phosphine compound is a monodentate ligand represented by the following formula (III):

PR¹R²R³                                (III)

wherein R¹, R² and R³ may be the same or different and each represents an optionally substituted alkyl group, an optionally substituted aralkyl group or an optionally substituted aryl group;
or a bidentate ligand represented by the following formula (IV):

R⁴R⁵P—A¹—PR⁶R⁷                         (IV)

wherein R⁴, R⁵, R⁶ and R⁷ may be the same or different and each represents an optionally substituted alkyl group, an optionally substituted aralkyl group or an optionally substituted aryl group; and A¹ represents an optionally substituted alkylene group, —A²—Ar—Ar—A²— or —Ar—Ar, wherein A² represents an optionally substituted alkylene group, and —Ar—Ar— represents a 1,1'-biphenyl group having a bond at the 2,2'-position, a 1,1'-binaphthyl group having a bond at the 2,2'-position, or a 5,5',6,6',7,7',8,8'-octahydro-1,1'-binaphthyl group having a bond at the 2,2'-position, wherein the biphenyl group may be substituted by a methyl, methoxy or dialkyl-substituted amino group and the binaphthyl group may be substituted by an alkali sulfonate.

4. The process for producing trans-3-isocamphylcyclohexanol as claimed in claim 1, wherein the ruthenium/phosphine complex has an auxiliary ligand selected from the group consisting of 1,5-cyclooctadiene, benzene, p-cymene, acetonitrile, benzonitrile, pyridine, quinoline, isoquinoline, acetic acid and acetylacetonate.

5. The process for producing trans-3-isocamphylcyclohexanol as claimed in claim 1, wherein the ruthenium/phosphine complex is selected from the group consisting of complexes 1 to 4 represented by the following formulae (V) to (VIII):

Complex 1: RuH_a(X¹)_bL_c            (V)

wherein X¹ represents a halogen atom or a group represented by "R⁸COO", wherein R⁸ represents a hydrogen atom, an alkyl group having from 1 to 4 carbon atoms or a halogenated alkyl group having from 1 to 4 carbon atoms; L represents an organic phosphine compound; a and b are each an integer of from 0 to 2, provided that (a+b) is 2; when L is monodentate ligand, c is an integer of from 3 to 4; and when L is bidentate ligand, c is an integer of from 1 to 2;

Complex 2: (RuH_dL_e)(X²)_f           (VI)

wherein X² represents ClO₄, PF₆ or BF₄; L is as defined above; when L is monodentate ligand, e is 2 and f is 2 when d is 0; and e is 4 and f is 1 when d is 1; and when L is bidentate ligand, e is 1 and f is 2 when d is 0; and e is 2 and f is 1 when d is 1;

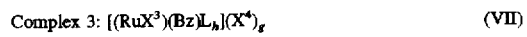

Complex 3: [(RuX³)(Bz)L_h](X⁴)_g      (VII)

wherein X³ represents a halogen atom; Bz represents optionally substituted benzene; X⁴ represents a halogen atom, ClO₄, PF₆, BF₄ or BPh₄, wherein Ph represents a phenyl group, the same will apply hereinafter; L is as defined above; when L is monodentate ligand, h is 2 and g is 1 or g may be 3 when X³ and X⁴ are each an iodine atom; and when L is bidentate ligand, h is 1 and g is 1 or g may be 3 when X³ and X⁴ are each an iodine atom; and

Complex 4: (Ru₂Cl₄L_w)(T)             (VIII)

wherein T represents a tertiary amine; and L is as defined above; when L is monodentate ligand, w is 4; and when L is bidentate ligand, w is 2.

6. The process for producing trans-3-isocamphylcyclohexanol as claimed in claim 1, wherein the base containing an alkali metal or an alkaline earth metal is a compound represented by the following general formula (IX):

M(R⁹)                                  (IX)

wherein M represents an alkali metal or an alkaline earth metal; and R⁹ represents a hydroxyl group, an alkoxy group having from 1 to 4 carbon atoms or a mercapto group.

7. The process for producing trans-3-isocamphylcyclohexanol as claimed in claim 1, wherein the base containing an alkali metal or an alkaline earth metal is employed in an amount of from about 0.5 to 100 equivalents to the complex.

8. The process for producing trans-3-isocamphylcyclohexanol as claimed in claim 1, wherein the amine is selected from the group consisting of primary, secondary or tertiary amines represented by the following general formula (X):

NR¹⁰R¹¹R¹²                             (X)

wherein R¹⁰, R¹¹ and R¹² are the same or different and each represents a hydrogen atom, an optionally substituted alkyl group, an optionally substituted aralkyl group or an optionally substituted aryl group, provided that R¹⁰, R¹¹ and R¹² do not represent hydrogen atoms at the same time;
primary, secondary or tertiary diamines represented by the following general formula (XI):

NR¹³R¹⁴—Z—NR¹⁵R¹⁶                      (XI)

wherein R¹³, R¹⁴, R¹⁵ and R¹⁶ are the same or different and each represents a hydrogen atom, an optionally substituted alkyl group, an optionally substituted aralkyl group or an optionally substituted aryl group; and Z represents an optionally substituted, saturated or unsaturated carbon chain having from 1 to 6 carbon atoms or an optionally substituted, saturated or unsaturated carbon ring having from 3 to 6 carbon atoms; and other cyclic amines.

9. The process for producing trans-3-isocamphylcyclohexanol as claimed in claim 1, wherein the amine is employed in an amount of from about 1 to 8 equivalents to the complex (in the case of a monoamine), or from about 0.5 to 4 equivalents to the complex (in the case of a diamine).

10. The process for producing trans-3-isocamphylcyclohexanol as claimed in claim 1, wherein the molar ratio of the 3-isocamphylcyclohexanone to the catalyst ranges from about 1/5 to 1/100,000.

11. The process for producing trans-3-isocamphylcyclohexanol as claimed in claim 1, wherein the molar ratio of the 3-isocamphylcyclohexanone to the catalyst ranges from about 1/200 to 1/50,000.

* * * * *